United States Patent
Droin et al.

(10) Patent No.: US 10,514,288 B2
(45) Date of Patent: Dec. 24, 2019

(54) METER AND METHOD FOR DETECTON OF A METER HAVING BEEN TAMPERED WITH

(71) Applicant: Itron Global SARL, Liberty Lake, WA (US)

(72) Inventors: Frederic Droin, Liergues (FR); Michel Esteves, Chanes (FR); Rivory Philippe, Macon (FR)

(73) Assignee: Itron Global SARL, Liberty Lake, WA (US)

( * ) Notice: Subject to any disclaimer, the term of this patent is extended or adjusted under 35 U.S.C. 154(b) by 160 days.

(21) Appl. No.: 15/721,031

(22) Filed: Sep. 29, 2017

(65) Prior Publication Data

US 2018/0023989 A1    Jan. 25, 2018

Related U.S. Application Data

(63) Continuation of application No. PCT/EP2016/057019, filed on Mar. 31, 2016.

(30) Foreign Application Priority Data

Apr. 2, 2015  (EP) .................... 15290091

(51) Int. Cl.
*G01F 15/00* (2006.01)
*G01N 29/02* (2006.01)
*G01N 29/024* (2006.01)

(52) U.S. Cl.
CPC ......... *G01F 15/007* (2013.01); *G01N 29/024* (2013.01); *G01N 2291/105* (2013.01)

(58) Field of Classification Search
None
See application file for complete search history.

(56) References Cited

U.S. PATENT DOCUMENTS

| 2007/0241930 A1* | 10/2007 | Qureshi | G01D 4/002 340/870.02 |
| 2012/0232915 A1* | 9/2012 | Bromberger | G01D 4/004 705/1.1 |

FOREIGN PATENT DOCUMENTS

| GB | 2209218 A | 4/1989 |
| GB | 2447903 A | 1/2008 |
| WO | WO2012129101 A1 | 9/2012 |
| WO | WO2012136209 A1 | 10/2012 |

OTHER PUBLICATIONS

EP Search Report dated Oct. 22, 2015 for EP Application No. 15290091.6, 8 pages.
PCTSearch Report dated Jul. 20, 2016 for PCT Application No. PCT/EP2016/057019, 12 pages.

* cited by examiner

*Primary Examiner* — Harshad R Patel
(74) *Attorney, Agent, or Firm* — Lee & Hayes, P.C.

(57) ABSTRACT

A method for detection of a utility meter having been tampered with, in particular a water or heat meter having been tampered with, and a meter for detecting such tampering are provided. The utility meter comprises a flow measurement portion in which the flow of water is measured. The method comprises detecting a presence of air in the flow measurement portion and evaluating a fraud condition, wherein the fraud condition comprises that air is present in the flow measurement portion for a first period of time or more. In response to the fraud condition being evaluated as met, an alert is generated.

20 Claims, 6 Drawing Sheets

METER AND METHOD FOR DETECTON OF A METER HAVING BEEN TAMPERED WITH

RELATED APPLICATIONS

This patent application is a continuation of and claims priority to PCT Application no. PCT/EP2016/057019, titled "A METER AND METHOD FOR DETECTION OF A METER HAVING BEEN TAMPERED WITH" filed on 31 Mar. 2016, which claims priority to EP Patent Application No. 15290091.6, titled "A METER AND METHOD FOR DETECTION OF A METER HAVING BEEN TAMPERED WITH" filed on 2 Apr. 2015, both of which are commonly assigned herewith and hereby incorporated by reference.

FIELD

The present disclosure relates to a method for detection of a utility meter having been tampered with, in particular a water or heat meter having been tampered with, and to a meter for detecting such tampering.

BACKGROUND

The amount of water supplied from the mains to a property may be measured using a water meter. The amount of water used is determined based on a meter reading and a customer is then charged a corresponding amount for the water supplied. Tampering of water meters such that the measured water used does not reflect the actual water used is a problem for water utility companies at least for the reason that this leads to a loss of revenue.

For meters equipped for Automatic Meter Reading (AMR), consumption, diagnostic and status data from the water meter may be automatically uploaded to a remote database for subsequent billing or other analysis over a communication network such as a fixed or wireless network, or by walk-by or drive-by meter reading. This has the advantage that the water company does not have to periodically visit each supplied property to carry out meter readings. Tampering of such meters can involve removing the meter from the mains network delivering water to the property such that water consumption is not accurately measured and hence data uploaded does not reflect actual water usage at the property. Since water companies have no need to visit each supplied property to take meter readings, this fraudulent use can often go undetected.

One approach to identify fraudulent use is to provide mechanical features on the meters, for example seals such that a broken seal indicates that the meter has been tampered with. However, this approach requires the water company to visit the property to inspect the meter and the seals which is both time consuming and costly. Another approach is to develop a consumption profile for the property and to identify potentially fraudulent use based on an amount of deviation from this profile. However, it is difficult to determine whether the meter has in fact been tampered with or whether there are other reasons for the deviation from the profile, for example, the occupant may have left the property for a period of time or the number of occupants may have changed. Therefore it is again difficult to determine whether the suspicions of tampering are well founded without inspecting the meter itself.

Accordingly, a means for detection of a water meter having been tampered with is required which addresses these problems.

SUMMARY

In a first aspect there is provided a method for detecting a utility meter having been tampered with, the meter comprising a flow measurement portion in which flow of water is measured, for example, a conduit through which liquid may flow. The method comprises detecting a presence of air in the flow measurement portion, evaluating a fraud condition wherein the fraud condition comprises that air is present in the flow measurement portion for a first period of time or more, for example a predetermined period of time, and generating an alert in response to the fraud condition being evaluated as met.

When a water meter is removed from a water mains network, air from the surrounding environment may enter the flow measurement portion. Hence the presence of air in the flow measurement portion for a first period of time or more may indicate that the meter has been removed from the water mains network and accordingly an alert is generated, for example an alarm is triggered. The flow measurement portion may be a pipe running through the meter such that water or another liquid may flow through the pipe.

By using such physical parameters associated with the meter which are measured at meter level, a more accurate determination of whether the meter has been removed from the water mains network may be obtained as compared with existing methods, for example by relying on consumption data. Further, in the case where air is present in the flow measurement portion for the first period of time or more and the meter has not been removed from the water mains network, this may indicate a problem with the meter which requires attention, providing another utility for this measure.

Accordingly, when an alert is generated, the utility company has more certainty that there is either fraudulent use of the meter or a fault with the meter, and hence that a visit to the property is required. Such increased certainty reduces the risk of unnecessary visits being made and hence saves both time and cost.

The first period of time for which air is present in the flow measurement portion may be between 5 and 60 seconds, between 5 and 30 seconds, between 5 and 20 seconds, for example between 5 and 15 seconds, for example 10 seconds.

Where a fraudulent user removes the meter from the water mains network, he or she may attempt to fill the meter, specifically the flow measurement portion, with water so to avoid air being detected in the flow measurement portion. Detecting a presence of air over a relatively short first period of time, e.g. 10 seconds, makes such filling of the meter difficult in the short time frame available. Hence, detection of fraud by the meter is improved.

Optionally, detecting the presence of air comprises detecting the presence of an amount of air greater than a given amount of air.

An ultrasonic flow sensor may be used to detect whether air is present in the flow measurement portion. Alternatively, any other suitable type of sensor may be used.

To evaluate if the fraud condition has been met, the duration for which air is detected in the flow measurement portion may be compared to the first period of time. The fraud condition may be evaluated as being met when the duration for which air is detected in the flow measurement portion is equal to or larger than the first period of time.

Detecting the presence of air in the flow measurement portion may comprise carrying out successive measurements to detect the presence of air, the successive measurements being carried out at a predetermined time interval, for example 1-10 seconds, for example 1-5 seconds, for example 2 seconds. In this way, a value corresponding to the number of measurements for which air has been detected in the flow measurement portion may be obtained which is indicative of the time period over which air is detected in the flow measurement portion. This value can then be compared to a threshold related to the first amount of time for which air is present in the flow measurement portion.

In some embodiments, when a presence of air is detected in the flow measurement portion for the first period of time or more, the method further comprises determining whether a presence of air is detected in the flow measurement portion some time later.

In some embodiments the fraud condition comprises that air is present in the flow measurement portion for the first period of time or more and for a second period of time or more.

In some embodiments the method comprises detecting a presence of air in the flow measurement portion of the first period of time or more, waiting for an interim period, and determining whether a presence of air is detected in the flow measurement portion for the second period of time or more.

The first period of time and the second period of time may be of equal direction.

In some embodiments, the detection principle used to detect a presence of air for the first and second periods of time is the same. This aids consistency of detection.

The interim period may be longer in duration than the first and the second periods of time, for example between 12 and 48 hours, for example between 12 and 24 hours, for example 24 hours. The interim period may be set by the utility company to be any suitable duration.

In an example embodiment, the method comprises detecting a presence of air in the flow measurement portion for a first period of 10 seconds, waiting for 24 hours, then determining whether air is present for a second period of 10 seconds.

The fraud condition may be evaluated as being met if a presence of air is detected in the flow measurement portion for both the first period of time and the second period of time.

Such detection of a presence of air both for the first period of time or more and for the second period of time or more may indicate that the meter has been removed from the water mains network and that air has entered the flow measurement portion as a result. Alternatively, such presence of air may indicate a fault with the meter that requires investigation. Either scenario is potentially of interest to a utility company.

The fraud condition may be evaluated as not being met if a presence of air is detected in the flow measurement portion for the first period of time or more but a presence of air is not detected in the flow measurement portion for the second period of time. This may indicate that air was only present in the flow measurement portion temporarily. This may be due, for example, to a temporary issue on the water mains network. Accordingly, determining a presence of air in the flow measurement portion for a first period of time or more and also for a second period of time or more reduces the occurrence of false alarms caused by temporary issues with the network.

The fraud condition may be evaluated as not being met if a presence of air is detected in the flow measurement portion for less than the first period of time. This facilitates the discounting of minor fluctuations in the water supply network.

In some embodiments, the method comprises measuring a pressure in the flow measurement portion. The fraud condition may comprise that the measured pressure is below a given pressure, for example, a predetermined pressure value.

In some embodiments the fraud condition comprises that the measured pressure is below a given pressure and/or that a presence of air is detected in the flow measurement portion for the first and/or second period of time or more.

In some embodiments, the method comprises detecting a presence of air in the flow measurement portion for the first period of time, determining whether air is present in the flow measurement portion for the second period of time and, where it is determined that air is not present for the second period of time, measuring the pressure in the flow measurement portion. In other words, the method may comprise measuring a pressure in the flow measurement portion in the event that a presence of air is detected in the flow measurement portion for the first period of time but not the second period of time Evaluating the fraud condition may comprise comparing the measured pressure to a given pressure. The fraud condition may be evaluated as being met when the pressure is found to be below the given pressure and/or when the presence of air is detected in the meter for more than the first and/or second period of time or more. For example, the fraud condition may be evaluated as being met when a presence of air is detected in the flow measurement portion for the first period of time, but not for the second period of time and the pressure is found to be below the given pressure.

When a water meter is removed from the water mains network, the pressure in the flow measurement portion will drop. Even if a fraudulent user fills the meter with water such that air is no longer present in the flow measurement portion, it is unlikely that he or she would be able to reproduce the water pressure present when the meter is connected to the mains network. Therefore when the pressure is below the threshold level, this may indicate that the meter has been removed from the network and hence an alert is generated.

The given pressure may relate to the known pressure on the water mains network, for example, an average water pressure of the water mains network.

In some embodiments, the fraud condition comprises more than one condition. For example, the fraud condition may comprise a first fraud condition and a second fraud condition.

The first fraud condition may comprise that air is present in the flow measurement portion for a first period of time and that the measured pressure is below a given pressure, for example, a predetermined pressure value. For example, the first fraud condition may comprise that air is present in the flow measurement portion for a first period of time, but not for the second period, and that the measured pressure is below a given pressure. The second fraud condition may comprise that air is present in the flow measurement portion for both the first period of time and the second period of time.

The fraud condition may be evaluated as being met when either the first fraud condition or the second fraud condition is evaluated as being met. The first fraud condition may be evaluated as being met when a presence of air is detected in the flow measurement portion for the first period of time or more and the pressure in the flow measurement portion is detected to be below the given pressure value. For example, the first fraud condition may be evaluated as being met when a presence of air is detected in the flow measurement portion for a first period of time, but not for the second period of time, and the pressure is detected to be below the given pressure value. The second fraud condition may be evaluated as being met when a presence of air is detected in the flow measurement portion for both a first and second period of time.

In the case where a presence of air is detected for a first period of time but not detected for a second period of time following an interim period, as described above, this may be due to a temporary issue on the water mains network. However this may also be due to fraudulent use of the meter in which a fraudulent user has removed the water meter from the water mains network and subsequently filled the meter with water in an attempt to avoid a presence of air in the flow measurement portion being detected. By determining whether the water pressure in the flow measurement portion is below a given threshold, it is possible to distinguish between these two potential causes. If the water pressure is determined to be above the given threshold, for example, the known pressure on the network, this suggests that the water meter is on the network and that the temporary presence of air in the flow measurement portion is due to a temporary issue with the network. If on the other hand the water pressure is determined to be below the given threshold, this indicates that the meter has been removed from the network. It is difficult for a fraudulent user to maintain the water pressure in the meter at the level present in the water mains network, therefore by carrying out the supplementary test of determining the water pressure in the meter, it is possible to identify fraudulent use which may not be identified by detecting the presence of air alone.

The given pressure value may be between 1 bar and 5 bars, for example 2 bars.

In some embodiments, the method comprises evaluating an in-operation condition. Evaluating the fraud condition may only be carried out in response to the in-operation condition being evaluated as being met.

In cases where a meter is being installed, for example, false alarms may be triggered during the installation phase due to presence of air and atmospheric pressure conditions. Accordingly, by evaluating whether a meter is operational, in other words whether installation has been completed and the meter is now operational, prior to evaluating whether the fraud condition is met, such false alarms may be avoided.

The in-operation condition may be based on an amount of water which has flowed through the flow measurement portion, a duration for which a flow rate is measured in the flow measurement portion, or any combination of an amount of water which has flowed through the flow measurement portion and a duration for which a flow rate is measured in the flow measurement portion.

The method may comprise measuring an amount of water which has flowed through the flow measurement portion. The in-operation condition may comprise that the amount of water is a given amount or more, for example, a predetermined amount of water. Evaluating the in-operation condition may comprise comparing the measured amount of water with the given amount of water which has flowed through the meter. The in-operation condition may be evaluated as being met when the measured amount of water is greater than or equal to the given amount of water. Such a given amount of water is indicative of the meter being operational, for example, the predetermined amount may be between 0.5 m3 and 5 m3, for example 1 m3.

Optionally an ultrasonic flow sensor is used to determine the amount of water which has flowed through the flow measurement portion. Alternatively an electromagnetic flow sensor, or any other suitable type of flow sensor, may be used.

Optionally the method comprises measuring a flow rate of water which has flowed through the meter. The in-operation condition may comprise that the duration for which a flow rate has been measured is a given duration or more, for example, a predetermined duration. Evaluating the in-operation condition may comprise comparing a duration for which a flow rate of water through the meter has been measured with the given duration. The in-operation condition may be evaluated as being met when the meter has measured a flow rate for the given duration of time or more. Such a given duration is indicative of the meter being operational and may be, for example, 12-48 hours, for example, 24 hours.

Optionally an ultrasonic flow sensor is used to measure a flow rate of water through the meter. Alternatively an electromagnetic flow sensor, or any other suitable type of flow sensor, may be used.

In some embodiments, the presence of air in the flow measurement portion, the flow rate of water through the flow measurement portion and/or the amount of water which has passed through the flow measurement portion are measured using a common signal transducer e.g. an ultrasonic signal transducer.

The first amount of time for which air is present in the flow measurement portion, the second period of time for which a presence of air in the flow measurement portion is determined, the given pressure value in the flow measurement portion, the given amount of water which has flowed through the flow measurement portion and/or the given flow duration for which a flow rate is measured in the flow measurement portion may comprise a threshold which is a fixed value or a threshold which may be adjusted dynamically.

One or more of the thresholds may be adjusted dynamically in response to conditions relating to the water mains network, for example supply conditions such as whether the meter is likely to be experiencing an intermittent supply from the network, or operations active on the network such as maintenance. In this way, the thresholds can be tailored to the conditions of the network.

In some embodiments, additional parameters associated with the meter may be determined and used to evaluate the fraud condition. For example a temperature in the flow measurement portion, for example the temperature of the water flowing through the flow measurement portion, may be measured. The fraud condition may further comprise that the measured temperature is above (or in alternative embodiments below) a given threshold. Hence the fraud condition will be evaluated as met if, in addition to the other requirements of the fraud condition being satisfied, the measured temperature is above (or in alternative embodiments below) the threshold. Such additional requirements provide more accurate tamper detection and reduce the occurrence of false alarms.

The fraud condition may comprise a plurality of fraud sub-conditions such that the fraud condition is evaluated as being met when any of the fraud sub-conditions are evaluated as having been met. The fraud condition or sub-conditions may comprise any suitable combination of requirements relating to a duration for which a presence of air is detected, a detected water pressure, and/or a detected temperature, for example.

Generating an alert may comprise triggering an alarm. In some embodiments, generating an alert comprises generating data or a message indicative of an alert condition, for example, such data or message may be communicated to the utility company.

The utility company may have information about the state of the water mains network such that it may be possible to account for false alarms remotely based on this information. In some embodiments the method further comprises enabling/disabling functions to avoid false alarms. This allows false alarms to be prevented by switching the alarm function off based on, for example, the above information.

The alert may be generated and/or reset at the meter itself, or at a site remote from the meter, for example, at an office of the utility company.

One or more of the thresholds may be adjusted dynamically in response to conditions relating to the location of the meter, for example, the meter may be in a location with intermittent water supply such as a location in which roof tanks are provided.

One or more of the thresholds (or parameters for dynamically setting them) may be set by the meter manufacturer or by a utility company. The thresholds may be set using any means of configuring the meter, for example, using a field tool, drive-by or walk-by methods.

In a second aspect a meter is provided for detecting that the meter has been tampered with, wherein the meter comprises a flow measurement portion, a flow sensor for measuring water in the flow measurement portion, an air detector for detecting a presence of air in the flow measurement portion, and a processor, and wherein the meter is arranged to implement a method as described above.

The meter may comprise a sensor for detecting pressure conditions in the flow measurement portion. For example, the pressure sensor may be a piezzo-resistive or piezzo-capacitive sensor.

In some embodiments, the pressure sensor operates based on a resistance bridge measurement.

The pressure sensor may be formed from a material which satisfies water regulations and/or can withstand chemical attacks.

In some embodiments, the flow sensor and the air detector comprise the same sensing arrangement, for example, the flow sensor and the air detector may comprise a common signal transducer e.g. an ultrasonic signal transducer.

In some embodiments, the meter is an ultrasonic meter having a flow sensor comprising an ultrasonic flow sensor. The ultrasonic flow sensor may also act as the air detector.

In some embodiments, the meter has an integrated pressure sensor.

In some embodiments the meter comprises a temperature sensor.

In some embodiments, the meter is a water meter for measuring water consumption. In other embodiments, the meter is a heat meter comprising a temperature sensor which is used, together with the flow sensor, to determine an amount of heat delivered to a property.

In some embodiments, the meter is arranged to receive updated parameters relating to the or each threshold.

The meter may comprise a communication unit arranged to communicate with a utility supply company. Such communication may comprise any suitable communication means, for example, wired or wireless communication and may comprise two-way communication between the meter and utility company.

An alert generated by the meter may be communicated to the utility company via the communication means. In some embodiments, the meter is arranged such that the fraud detection facility may be disabled, for example, by the utility company. This may be desirable in cases where there are a large number of false alarms, for example, where there is an intermittent water supply from the network to the meter.

BRIEF DESCRIPTION OF DRAWINGS

Specific embodiments are described below by way of example only and with reference to the accompanying drawings in which.

SPECIFIC DESCRIPTION OF AN EXAMPLE EMBODIMENT

Figure 1:
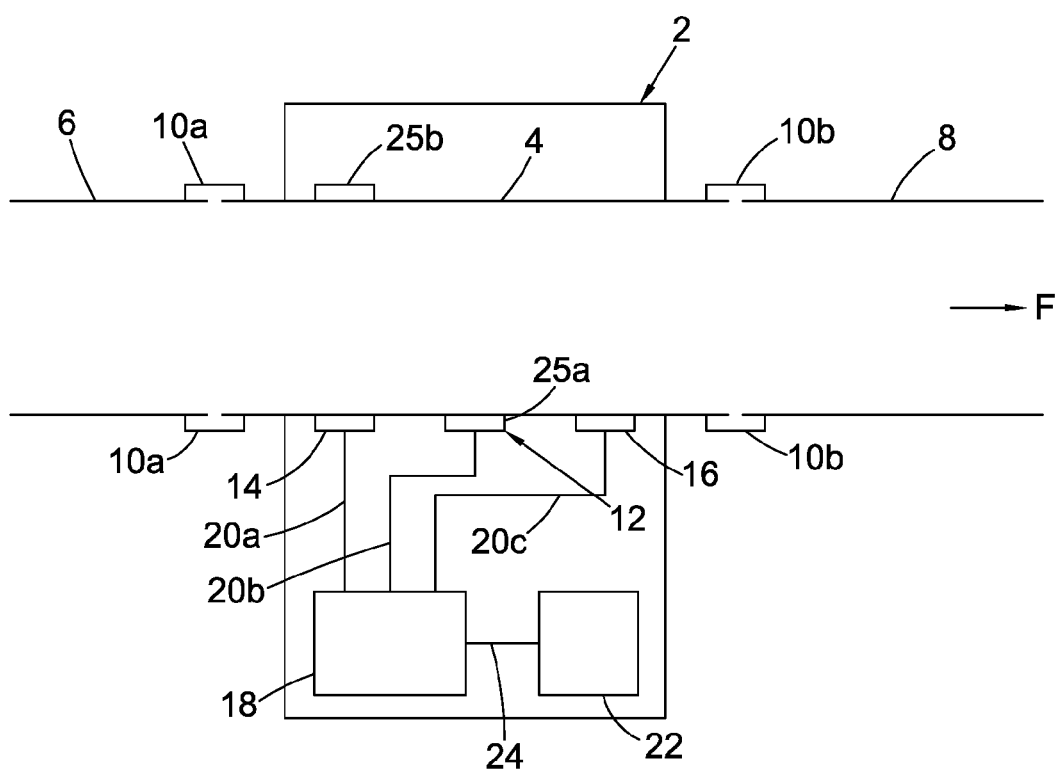
FIG. 1 is a schematic diagram illustrating a meter for detecting tampering with the meter.

A utility meter 2 is now described with reference to FIG. 1. The meter 2 is fitted via a pipe 4, providing a flow measurement portion, that runs through the meter to a pipe 6 bringing water from a supply network and a pipe 8 taking water into a property. Seals 10a, 10b are provided where the pipes join as can be seen in FIG. 1.

The meter 2 is provided with sensors comprising an ultrasonic flow sensor 12 and a water pressure sensor 14. In some embodiments, for example in the case where the utility meter is a heat meter, a temperature sensor 16 is also provided.

The sensors 12, 14 (and optionally 16) are coupled to a processor 18 via connections 20a, 20b (optionally 20c in the case of a heat meter) such that data from the sensors may be passed to the processor 18. Data received by the processor 18 includes data used to determine the water usage at the property for billing, data used for evaluating an in-operation condition (as will be described below), and/or data used for evaluating a fraud condition (as will be described below). The pressure sensor 14 is typically a piezzo-resistive or piezzo-capacitive sensor.

Figure 2:
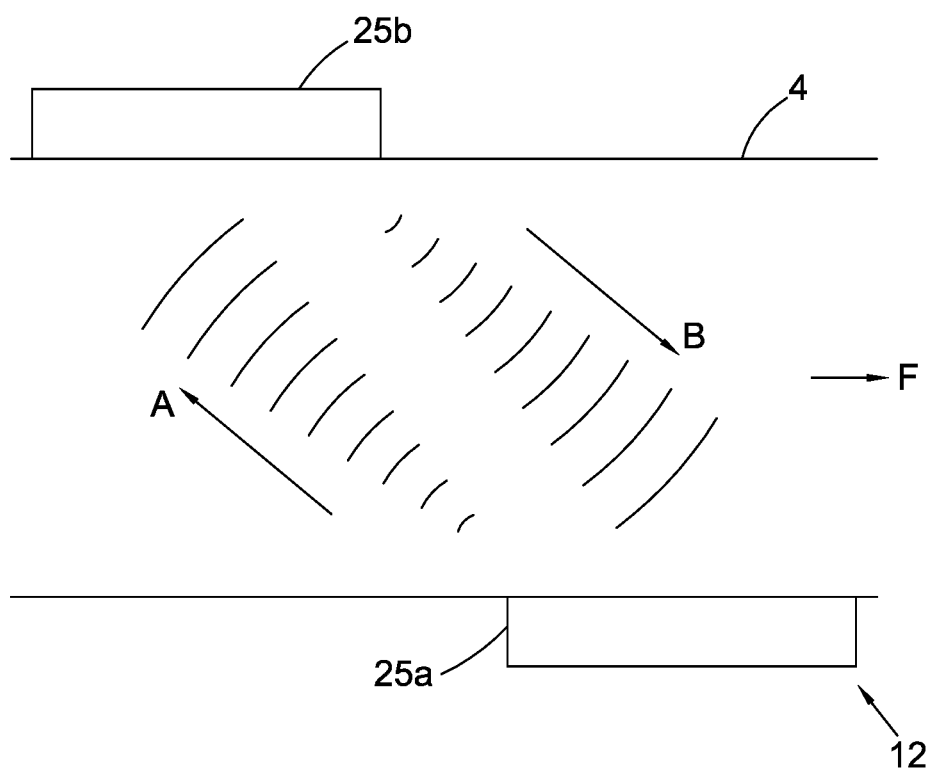
FIG. 2 is a schematic diagram illustrating an ultrasonic flow sensor.

With reference to FIG. 2, the flow sensor 12 comprises two ultrasound transceivers 25a, 25b positioned on either side of the pipe 4 and coupled to the processor 18 for calculation of a flow rate from transducer signals. Each of the two ultrasound transceivers 25a, 25b is configured to transmit and receive ultrasonic signals. Any other suitable sensor arrangement may be used.

The ultrasonic flow sensor 12 operates by measuring the difference in transmit time of ultrasonic pulses propagating along and against the direction of flow through the meter, shown by arrow 'F' in FIGS. 1 and 2. With reference to FIG. 2, a first ultrasonic pulse is transmitted from the first transceiver 25a in a direction against the direction of flow, shown by arrow 'A', and the ultrasonic pulse is received by the second transceiver 25b. The transmit time of this first pulse is measured. Similarly, a second ultrasonic pulse is transmitted from the second transceiver 25b in a direction along the direction of flow, shown by arrow 'B', and the ultrasonic pulse is received by the first transceiver 25a. The transmit time of this second pulse is also measured. By determining the difference in transmit time of the first and second pulses, the flow rate of the water passing through the meter can be determined. From this, the volume of water which has passed through the meter may also be calculated.

The transmit time of ultrasonic pulses will be different when travelling through air as compared to water and any presence of air in the sound path between the transceivers 25a, 25b will result in an impedance mismatch and reflections and hence a characteristic signature in the ultrasound signals. Accordingly, the flow sensor 12 is also used to detect the presence of air in the pipe 4 by detecting the characteristic signature in the ultrasound signals. Alternatively, a separate sensor to detect the presence of air in the pipe 4 may be used.

Referring back to FIG. 1, the processor 18 is coupled to a communication unit 22 via a connection 24. The processor 18 is configured to generate an alert, for example trigger an alarm (as will be described below), and communicate this to a water supply company via the communication unit 22. The communication unit 22 can communicate information to the water supply company via a suitable means, for example, wired or wireless communication. Similarly, the water supply company can communicate information to the communication unit 22, for example, information for use by the processor.

Figure 3:
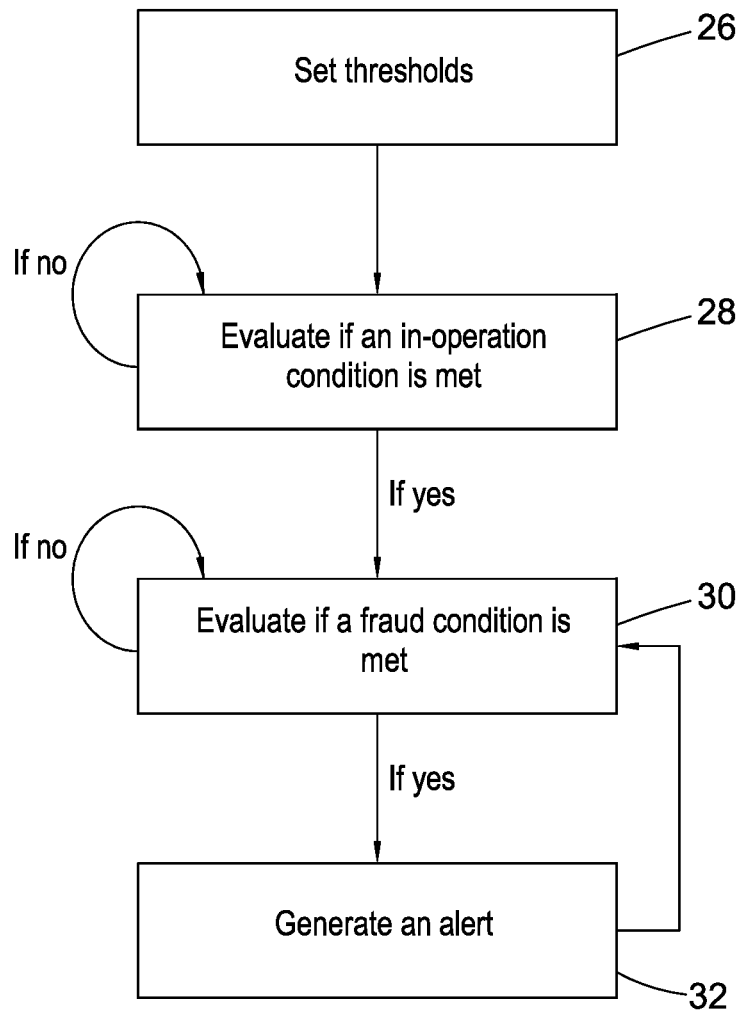
FIG. 3 is a flow chart illustrating a method for tamper detection of the meter.

The utility meter 2 is arranged to carry out a tamper detection process now described in overview with reference to FIG. 3. In a first step 26 a number of thresholds to be used in the method are set and stored on the processor 18 of the meter 2. These will be described in further detail below. In a second step 28, an "in-operation" condition is evaluated by the processor 18 until the processor determines that the condition is met. Once the in-operation condition is met, a fraud condition is evaluated by the processor at step 30 until it is determined that the fraud condition is met. Once the fraud condition is determined to be met, an alert is generated at step 32. When the alert is generated, the water supply company is alerted to suspected fraudulent use at the meter via the communication unit 22 and so can take appropriate action. The process may simply continue by looping back to evaluating if the fraud condition is met at step 30. This may involve a delay before evaluation resumes, in some embodiments.

Initially, five thresholds are set at step 26. These thresholds comprise a "first presence of air threshold", a "second presence of air threshold", a "water pressure threshold", a "water volume threshold" and a "water flow threshold". Taking each of these in turn, the "first presence of air threshold" relates to a duration for which air is detected in the pipe 4 and is typically 10 seconds. The "second presence of air threshold" relates to an additional period of time for which a presence of air is detected in the pipe 4. This is typically of the same duration as the first presence of air threshold and is typically 10 seconds. The "pressure threshold" relates to the measured pressure conditions in the pipe 4 and is typically 2 bars. The "water volume threshold" relates to an amount of water which has flowed through the pipe 4 and is typically 1 m3. The "water flow threshold" relates to the duration for which a flow rate through the pipe 4 is detected and is typically 24 hours.

The five thresholds are set by a water supply company and are adjusted dynamically and remotely from the meter to take account of known conditions in the water supply network, for example maintenance, so that the thresholds are not only set at step 26 but can also be remotely and dynamically set throughout the process, for example, at steps 28 or 30. Updated threshold information is communicated from the water supply company to the processor 18 via communication unit 22.

Figure 4:
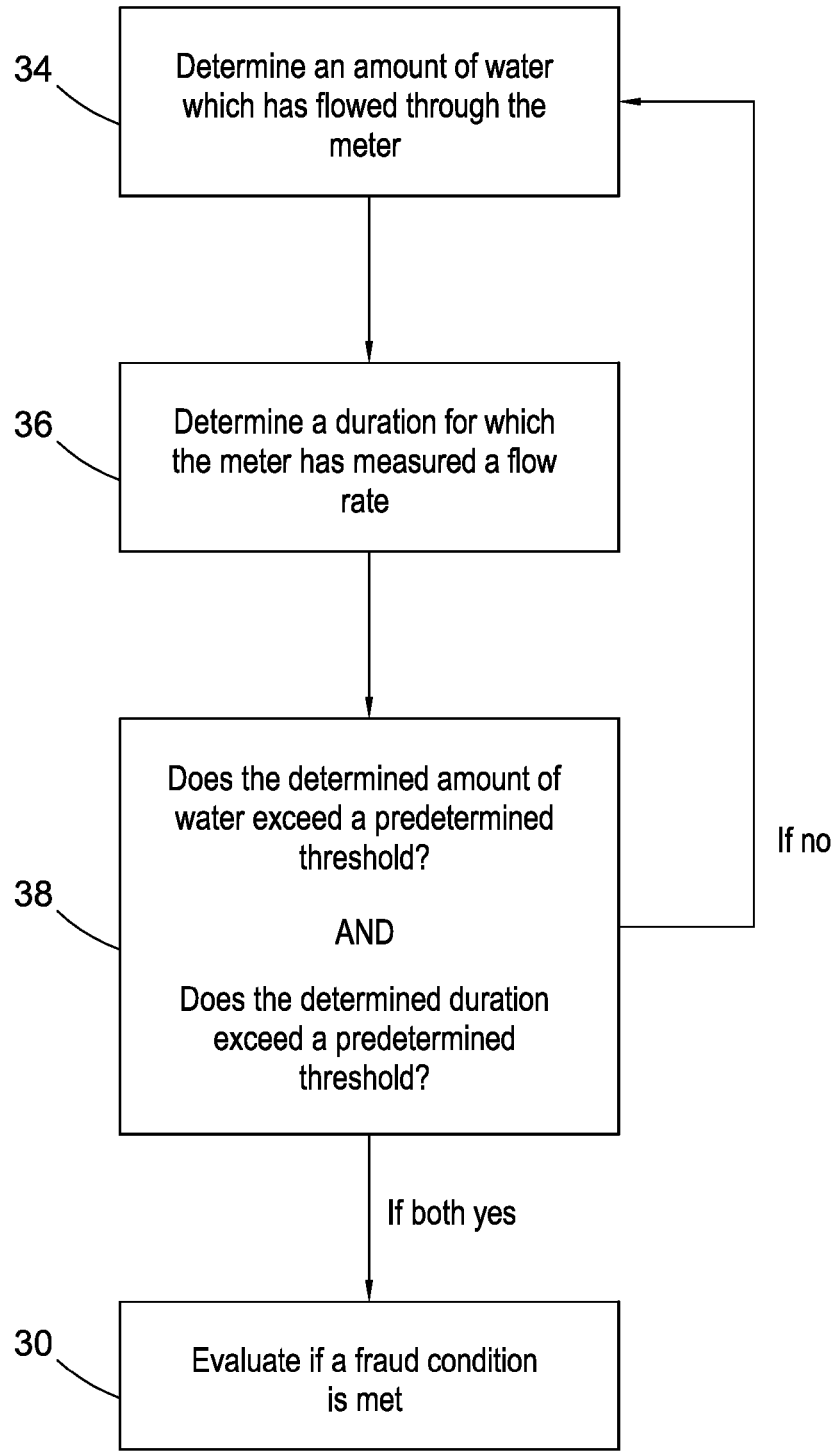
FIG. 4 is a flow chart detailing a step of evaluating if an in-operation condition is met in FIG. 3.

Once the thresholds have been set 26, an in-operation condition of the meter is evaluated 28 by the processor. This is now described in detail with reference to FIG. 4. When the in-operation condition is evaluated as being met, this indicates that installation of the meter has been completed and hence that the meter is operational.

To evaluate the in-operation condition, measurements are taken by the flow sensor 12 to determine, in a first step 34, an amount of water which has flowed through the pipe 4 and, in a second step 36, a duration for which a flow rate of water through the pipe 4 is measured. It will be understood that the order of these steps is of no consequence. The processor 18 compares the determined amount of water to the "water volume threshold" and the determined duration of flow to the "water flow threshold" at step 38. If both determined values meet or exceed their respective thresholds then the in-operation condition is evaluated to have been met and the method progresses to the evaluation of the fraud condition at step 30. If not, the process loops back to step 34 to be further commenced, optionally, after a predetermined amount of time has lapsed.

Figure 5:
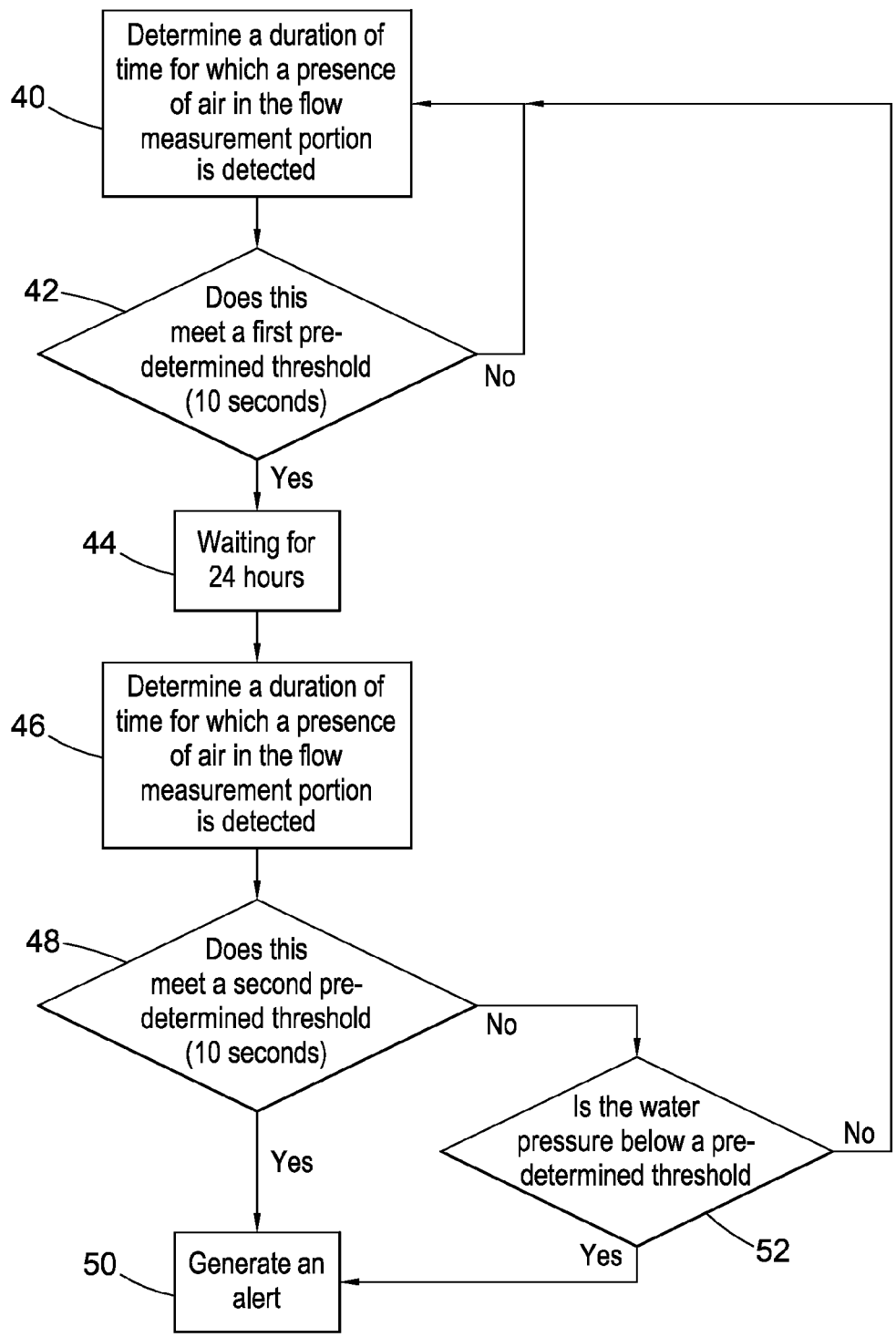
FIG. 5 is a flow chart detailing a step of evaluating if a fraud condition is met in FIG. 3.

Evaluation of a fraud condition is now described in detail with reference to FIG. 5. Firstly, measurements are made by the flow sensor 12 to determine whether air is present in the pipe 4.

Figure 6:
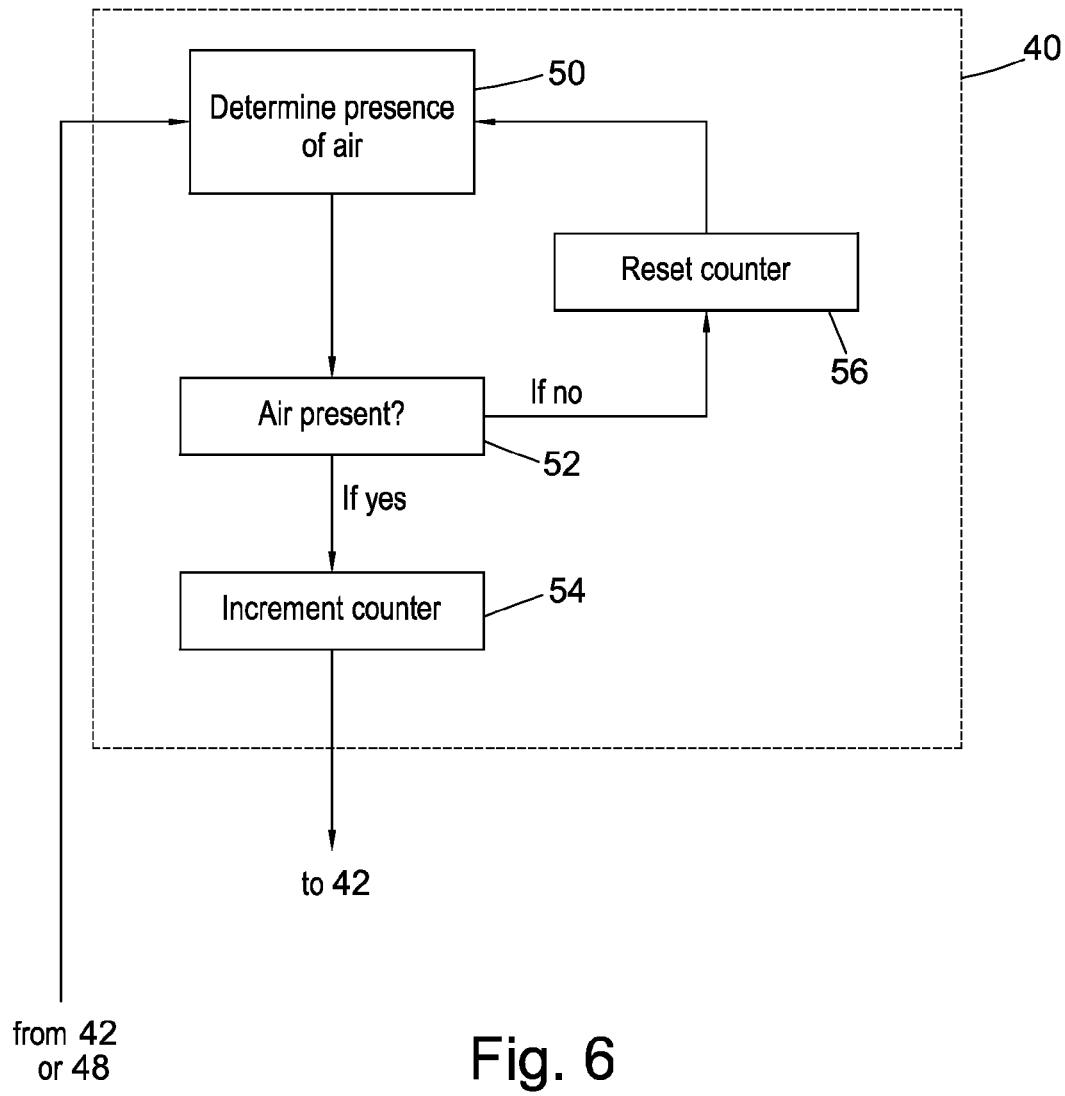
FIG. 6 is a flow chart detailing a step of determining a duration of time for which a presence of air is detected in the flow measurement portion.

Successive measurements are made with the flow sensor 12 at a predetermined time interval, for example at 2 second intervals, such that a value indicative of a duration throughout which air is detected in the pipe 4 is calculated by the processor at step 40. As shown in FIG. 6, to determine a duration for which air is detected in the pipe 4, it is first determined based on flow sensor 12 measurements whether a presence of air is detected in the pipe 4 at steps 50 and 52. If air is found to be present a counter is incremented 54 and the process proceeds to step 42. The value indicative of the duration throughout which air is detected in the pipe 4 is determined based on the value of the counter. If air is not found to be present the counter is reset 56 and the process loops back to step 50.

Referring again to FIG. 5, the calculated value is compared to the "first presence of air threshold" at step 42 and, if the threshold is met, the method proceeds to the next step 44. If the threshold is not met, the process loops back to step 40 to continue the process of determining the duration of time for which a presence of air is detected, optionally, after a predetermined amount of time has lapsed.

At step 44 the process is paused for an interim period of time. Typically step 44 comprises waiting for a period of 24 hours, before proceeding to step 46.

At step 46, measurements are made by the flow sensor to determine whether air is present in the pipe 4. As at step 40, successive measurements are made with the flow sensor 12 at a predetermined time interval, e.g. 2 seconds, such that a second value indicative of second duration throughout which air is detected in the pipe 4 is calculated. The second value is compared to the "second presence of air threshold at step 48". If the threshold is met, an alert is generated 50. If the threshold is not met the method proceeds to step 52.

At step 52 the pressure sensor 14 is used to measure the pressure conditions in the pipe 4. The processor 18 compares the measured pressure to the "pressure threshold" and, if the measured pressure is below the threshold, an alert is generated at step 50. If the measured pressure is above the threshold, this may indicate that the meter is still attached to the water supply network, and hence that fraudulent use is not taking place, and so an alert is not generated. By carrying out this complimentary test it is possible to identify fraudulent use which may not be identified by detecting the presence of air alone.

If the pressure is above the threshold the process loops back to step 40 to continue the process of determining a duration for which a presence of air is detected in the pipe 4. It will be understood that these steps implement a first and second fraud condition and that an alert is generated when either of these conditions are met. The first fraud condition requires that air is present in the pipe 4 for a duration which meets the "first presence of air threshold" and for a duration which meets the "second presence of air threshold". The second condition requires that air is present in the pipe 4 for a duration which meets the "first presence of air threshold" and that the water pressure is below the pressure threshold", i.e. "second presence of air threshold" is not met. It will be understood that the first and second fraud conditions comprise an "AND" condition when both the conditions must be met to generate an alert. It will be understood that the specific order of steps is not the only order to achieve this.

When the alert is generated, this is communicated from the meter to the utility supply company via the communication unit 22 such that the utility supply company is alerted to suspected fraudulent use at the meter and so can take action. For example, such an alert may be in the form of data or a message indicative of an alert. Once the appropriate action has been taken, or if it is decided that no action should be taken, the process proceeds to evaluate if the fraud condition has been met, optionally, after a predetermined amount of time has lapsed.

Processor 18 represents one or more general-purpose processors such as a microprocessor, central processing unit, or the like. More particularly, the processor 18 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 18 may also be one or more special-purpose processing devices such as an application specific integrated circuit (ASIC), a field programmable gate array (FPGA), a digital signal processor (DSP), network processor, or the like. Processor 18 is configured to execute the processing logic (e.g. instructions for the tamper detection process) for performing the operations and steps discussed herein.

The utility meter 2 may further include a display unit (e.g., a liquid crystal display (LCD)), an alphanumeric input device (e.g., a keyboard or touchscreen), a cursor control device (e.g., a touchscreen), and an audio device (e.g., a speaker). The utility meter 2 may also include a data storage device comprising one or more machine-readable storage media (or more specifically one or more non-transitory computer-readable storage media) on which is stored one or more sets of instructions (e.g. instructions for the tamper detection process) embodying any one or more of the methodologies or functions described herein. The instructions may also reside, completely or at least partially, within the main memory and/or within the processor 18 during execution thereof by the utility meter 2, the main memory and the processor 18 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, any features described above can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware module may be or include a special-purpose processor, such as a field programmable gate array (FPGA) or an ASIC. A hardware module may also include programmable logic or circuitry that is temporarily configured by software to perform certain operations.

In addition, the features described above can be implemented as firmware or functional circuitry within hardware devices. Further, the modules can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It will be understood that the above description is of specific embodiments by way of example only and that many modifications and alterations will be within the skilled person's reach and are intended to be covered by the scope of the appendent claims. For example, it will be apparent that all five thresholds need not be set at the start of the method. In some embodiments the "first presence of air threshold", "second presence of air threshold" and "water pressure threshold" may be set once the in-operation condition has been met. In some embodiments, generating the alert may take place remote from the meter. It will also be appreciated that the methods and meters described herein are applicable to any liquid being supplied and so this disclosure should not be considered as limiting to meters for water supply. In particular, the described method may be applied to heat meters that measure water flow and temperature to determine consumption of remotely provided heat.

The invention claimed is:

1. A method for detecting a utility meter having been tampered with, the utility meter comprising a flow measurement portion in which flow of water is measured, the method comprising:

detecting, by an ultrasonic signal transducer, a presence of air in the flow measurement portion;

evaluating a fraud condition, wherein the fraud condition comprises that air is present in the flow measurement portion for a first period of time or more; and generating an alert in response to the fraud condition being evaluated as met.

2. A method according to claim 1, wherein the fraud condition comprises that air is present in the flow measurement portion for the first period of time or more and for a second period of time or more.

3. A method according to claim 1, wherein, after detecting the presence of air in the flow measurement portion, the method further comprises waiting for an interim period of time and determining a presence of air in the flow measurement portion for a second period of time.

4. A method according to claim 1, wherein the fraud condition comprises a first fraud sub-condition and a second fraud sub-condition, the first fraud sub-condition comprising that air is present in the flow measurement portion for both the first period of time or more and a second period of time or more, the second fraud sub-condition comprising that air is present in the flow measurement portion for the first period of time or more and that a pressure in the flow measurement portion is below a given pressure.

5. A method according to claim 1, wherein the method comprises measuring a pressure in the flow measurement portion and wherein the fraud condition further comprises that the pressure in the flow measurement portion is below a given pressure.

6. A method according to claim 1, wherein the method comprises evaluating an in-operation condition, wherein the in-operation condition is indicative of the utility meter being operational, and wherein evaluation of the fraud condition is carried out in response to the in-operation condition being evaluated as met.

7. A method according to claim 1, wherein the first period of time for which air is present, a second period of time for which air is present, and/or a pressure within the flow measurement portion is adjusted dynamically in response to conditions of a water mains network.

8. A utility meter having a processor for detecting that the utility meter has been tampered with, wherein the utility meter comprises a flow measurement portion, an ultrasonic signal transducer for measuring water flow in the flow measurement portion and for detecting a presence of air in the flow measurement portion, and wherein the processor is arranged to:

evaluate a fraud condition, wherein the fraud condition comprises that air is present in the flow measurement portion for a first period of time or more; and generate an alert in response to the fraud condition being evaluated as met.

9. A utility meter according to claim 8, wherein the fraud condition comprises that air is present in the flow measurement portion for the first period of time or more and for a second period of time or more.

10. A utility meter according to claim 8, wherein the utility meter is arranged to detect the presence of air in the flow measurement portion for the first period of time and, following an interim period of time, to determine the presence of air for a second period of time.

11. A utility meter according to claim 8, wherein the fraud condition comprises a first fraud sub-condition and a second fraud sub-condition, the first fraud sub-condition comprising that air is present in the flow measurement portion for both the first period of time or more and a second period of time or more, the second fraud sub-condition comprising that air is present in the flow measurement portion for the first period of time or more and that a pressure in the flow measurement portion is below a given pressure.

12. A utility meter according to claim 8, wherein the utility meter comprises a pressure sensor for sensing a pressure in the flow measurement portion and wherein the fraud condition further comprises that the pressure in the flow measurement portion is below a given pressure.

13. A utility meter according to claim 8, wherein the processor is arranged to evaluate an in-operation condition, wherein the in-operation condition is indicative of the utility meter being operational, and wherein the processor is arranged to evaluate the fraud condition in response to determining that the in-operation condition is met.

14. A utility meter according to claim 8, wherein the utility meter is arranged to receive updated parameters relating to the first period of time for which air is present, a second period of time for which air is present, and/or a given pressure.

15. A method for detecting a utility meter having been tampered with, comprising:

determining a first duration of time for which air is detected in a flow measurement portion of the utility meter is detected;

determining that the first duration of time exceeds a first threshold;

based at least in part on the first threshold being exceeded, entering a waiting period;

following the waiting period, determining a second duration of time for which air is detected in the flow measurement portion of the utility meter is detected;

determining that the second duration of time exceeds a second threshold; and based at least in part on the second threshold being exceeded, generating an alert indicating a fraud condition.

16. The method according to claim 15, additionally comprising:

repeating the determining of the first duration of time for which air is detected in the flow measurement portion of the utility meter is detected.

17. The method according to claim 15, wherein generating the alert is additionally based at least in part on determining if water pressure within the utility meter is below a third threshold.

18. The method according to claim 15, wherein:
the first threshold is between 5 and 60 seconds; and
the waiting period is between 12 and 48 hours.

19. The method according to claim 15, wherein at least one of the first threshold or the second threshold is selected to be less than a time required to fill the utility meter with water received from an inlet.

20. The method according to claim 15, wherein at least one of the first threshold or the second threshold is based at least in part on a time required to fill the utility meter with water received from an inlet.

* * * * *